US005888739A

United States Patent [19]
Pitner et al.

[11] Patent Number: 5,888,739
[45] Date of Patent: *Mar. 30, 1999

[54] DETECTION OF NUCLEIC ACIDS USING G-QUARTETS AND I-TETRAPLEXES

[75] Inventors: J. Bruce Pitner, Durham; James G. Nadeau, Chapel Hill; Glenn P. Vonk, Fuquay-Varina, all of N.C.

[73] Assignee: Becton, Dickinson and Company, Franklin Lakes, N.J.

[*] Notice: The term of this patent shall not extend beyond the expiration date of Pat. No. 5,691,145.

[21] Appl. No.: 926,054

[22] Filed: Sep. 9, 1997

Related U.S. Application Data

[63] Continuation-in-part of Ser. No. 703,755, Aug. 27, 1996, Pat. No. 5,691,145.

[51] Int. Cl.$^6$ .............................. C12Q 1/68; C07H 21/04
[52] U.S. Cl. ...................... 435/6; 536/24.3; 536/24.31; 536/24.32; 536/24.33
[58] Field of Search ................... 435/6, 24.31; 536/24.3, 536/24.32, 24.33; 935/77, 78

[56] References Cited

U.S. PATENT DOCUMENTS

| | | | |
|---|---|---|---|
| 4,996,143 | 2/1991 | Heller et al. ................................. | 435/6 |
| 5,691,145 | 11/1997 | Pitner et al. ................................ | 435/6 |

OTHER PUBLICATIONS

L. E. Morrison and L. M. Stols "Sensitive Fluorescence-–Based Thermodynamic and Kinetic Measurements of DNA Hybridization in Solution" Biochem. 32:3095–3104 (1993).
K. M. Parkhurst and L. J. Parkhurst "Kinetic Studies by Fluorescence Resonance Energy Transfer Employing a Double–Labeled Olifonucleotide: Hybridization to the Oligonucleotide Complement and to Single–stranded DNA" Biochem. 34:285–292 (1995).
J. P. Cooper and P. J. Hagerman "Analysis of Fluorescence Energy Transfer in Duplex and Branched DNA Molecules" Biochem. 29:9261–9268 (1990).
L. B. McGown, et al. "The Nucleic Acid Ligand—A new Tool for Molecular Recognition" Anal. Chem. Nov. 1, 1995. pp. 663A–668A.
M. F. Kubik, et al. "High–affinity RNA ligands to human α–thrombin" Nucl. Acids Res. 22:2619–2626 (1994).
W. Bannwarth, et al. "Energy Transfer within Oligonucleotides froma Lumazine (=Pteridine–2,4(1H,3H)–dione) Chromophore to Bathophenanthroline–ruthenium(II) Complexes" Helv. Chim. Acta 74:1991–1999 (1991).
J–L. Mergny, et al. "Fluorescence Engergy Transfer between Two Triple Helix–Forming Oligonucleotides Bound to Duplex DNA" Biochem. 33:15321–15328 (1994).

R. A. Cardullo, et al. "Detection of nucleic acid hybridization by nonradiative fluorescence resonance energy transfer" Proc. Natl. Acad. Sci. USA 85:8790–8794 (1988).
E. Dias, et al. "Chemical Probe for Glycosidic Conformation in Telomeric DNAs" J. Am. Chem. Soc. 116:4479–4480 (1994).
K. Y. Wang, et al. "A DNA Aptamer Which Binds to and Inhibits Thrombin Exhibits a New Structural Motif for DNA" Biochem. 32:1899–1904 (1993).
R. F. Macaya, et al. "Thrombin–binding DNA aptamer forms a unimolecular quadruplex structure in solution" Proc. Natl. Acad. Sci. USA 90:3745–3749 (1993).
P. Schultze, et al. "Three–dimensional Solution Structure of the Thrombi–binding DNA Aptamer d(GGTTGGTGTGGT-TGG)" J. Mol. Biol. 235:1532–1547 (1994).
J. A. Kelly, et al. "Reconciliation of the X–ray and NMR Structures of the Thrombin–Binding Aptamer d(GGTTG-GTGTGGTTGG)" J. Mol. Biol. 256:417–422 (1996).
L. C. Bock, et al. "Selection of single–stranded DNA molecules that bind and inhibit human thrombin" Nature 355:564–566 (1992).
Y. Wang and D. J. Patel "Solution structure of the human telomeric repeat d[AG$_3$(T$_2$AG$_3$)$_3$] G–tetraplex" Structure 1:263–282 (1993).
D. Rhodes and R. Giraldo "Telomere structure and function" Curr. Opin. Struct. Biol. 5:311–322 (1995).

*Primary Examiner*—Lisa B. Arthur
*Attorney, Agent, or Firm*—Donna R. Fugit

[57] ABSTRACT

G-quartet structures have been found to be useful in fluorescence assays to detect a selected nucleic acid sequence. When oligonucleotides containing these structures are labeled with a donor fluorophore and an acceptor dye, the folding or interaction of the oligonucleotides in the G-quartet structure brings the donor-acceptor pair into close proximity, allowing an interaction between the two labels which results in quenching of donor fluorescence or a change in other fluorescence properties which are the result of the interaction of two dyes in close proximity. The G-quartet structure unfolds or is otherwise disrupted upon hybridization to its complementary sequence, increasing the distance between the two dye labels. This results in decreased donor quenching or a change in another proximity-related fluorescence parameter. The associated increase in donor fluorescence intensity or the change in another fluorescence parameter may be monitored as an indication of the presence of a selected nucleic acid sequence. Alternatively, in some cases a decrease in acceptor fluorescence may be monitored as an indication of the presence of the selected nucleic acid sequence when the acceptor is also a fluorophore. Related structures, such as the i-tetraplex, may also be useful in similar methods for detection of a selected nucleic acid sequence.

23 Claims, 7 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 7..11
        ( D ) OTHER INFORMATION: /standard_name= "1-3 N may be missing"

( x i ) SEQUENCE DESCRIPTION: SEQ ID NO:1:

GGNTGGNNNN NGGNTGG                      1 7

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 3..12
        ( D ) OTHER INFORMATION: /standard_name= "1-8 N may be missing"

( i x ) FEATURE:
    ( A ) NAME/KEY: misc_feature
    ( B ) LOCATION: 15..24
    ( D ) OTHER INFORMATION: /standard_name= "1-8 N may be
        missing"

( i x ) FEATURE:
    ( A ) NAME/KEY: misc_feature
    ( B ) LOCATION: 27..36
    ( D ) OTHER INFORMATION: /standard_name= "1-8 N may be
        missing"

( x i ) SEQUENCE DESCRIPTION: SEQ ID NO:2:

GGNNNNNNNN NNGGNNNNNN NNNNGGNNNN NNNNNNGG        38

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

GGTTGGTGTG GTTGG        15

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

GGTTTTGGTT TTGGTTTTGG        20

( 2 ) INFORMATION FOR SEQ ID NO:5:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

GGTTGGTGTG GTTGGTCTAG AGTCTTCAAA TATCAGAGCT TTACCTAACA A        51

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

TTGTTAGGTA AAGCTCTGAT ATTTGAAG        28

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

GGTTGGTGTG GTTGGTTTAT CCGTATGGTG GATAACGTCT TTCA        44

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

GACGTTATCC ACCATACGG                                                        1 9

( 2 ) INFORMATION FOR SEQ ID NO:9:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear     ( i x ) FEATURE:
        ( A ) NAME/KEY: misc_feature
        ( B ) LOCATION: 4..13
        ( D ) OTHER INFORMATION: /standard_name= "1-8 N may be
            missing"

( i x ) FEATURE:
        ( A ) NAME/KEY: misc_feature
        ( B ) LOCATION: 17..26
        ( D ) OTHER INFORMATION: /standard_name= "1-8 N may be
            missing"

( i x ) FEATURE:
        ( A ) NAME/KEY: misc_feature
        ( B ) LOCATION: 30..39
        ( D ) OTHER INFORMATION: /standard_name= "1-8 N may be
            missing"

( x i ) SEQUENCE DESCRIPTION: SEQ ID NO:9:

GGGNNNNNNN NNNGGGNNNN NNNNNGGGN NNNNNNNNG GG                4 2

( 2 ) INFORMATION FOR SEQ ID NO:10:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

GGGTATATGG GTAATGGGTA TGGGTGTCTT CAAATATCAG AGCTTTACCT AACAA      5 5

( 2 ) INFORMATION FOR SEQ ID NO:11:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

GGTTGGCTCG AGGTTGGTTT ATCCGTATGG TGGATAACGT CTTTCA                4 6

DETECTION OF NUCLEIC ACIDS USING G-QUARTETS AND I-TETRAPLEXES

This is a continuation-in-part of application Ser. No. 08/703,755, filed Aug. 27, 1996, issued as U.S. Pat. No. 5,691,145 on Nov. 25,1997.

FIELD OF THE INVENTION

The present invention relates to materials and methods for detecting nucleic acids and in particular to materials and methods for detecting nucleic acids which employ a measurable change in fluorescence resulting from a change in the distance between two dye labels.

BACKGROUND OF THE INVENTION

Sequence-specific hybridization of oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) for detection of probe hybridization rather than direct detection of fluorescence intensity. Fluorescence energy transfer occurs between a donor fluorophore and an acceptor dye (which may or may not be a fluorophore) when the absorption spectrum of one (the acceptor) overlaps the emission spectrum of the other (the donor) and the two dyes are in close proximity. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Förster (1948. *Ann. Phys.* 2:55–75). The distance between donor and acceptor dyes at which energy transfer efficiency is 50% is referred to as the Förster distance ($R_O$). Other fluorescence properties may also be dependent on the proximity of a donor and an acceptor, e.g., fluorescence lifetime of the donor and/or acceptor, fluorescence polarization and fluorescence anisotropy.

Energy transfer and other mechanisms which rely on the interaction of two dyes in close proximity to produce a change in a fluorescence property are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogenous assays generally require additional steps to separate hybridized label from free label. Typically, FET and related methods have relied upon monitoring a change in the fluorecence properties of one or both dye labels when they are brought together by the hybridization of two complementary oligonucleotides. In this format, the change in fluorescence properties may be measured as a change in the amount of energy transfer or as a change in the amount of fluorescence quenching. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the acceptor. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352). Alternatively, the donor and acceptor may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer and quenching are decreased when the oligonucleotide is hybridized. For example, a self-complementary oligonucleotide labeled at each end forms a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. A "double hairpin" scheme is described by B. Bagwell, et al. (1994. *Nucl. Acids Res.* 22:2424–2425). Kramer and Tyagi (1996. *Nature* 14:303–308) describe a hairpin with the detector sequence in a loop between the arms of the hairpin.

Prior art methods may lack efficiency in the energy transfer itself, and it has often been difficult to achieve adequate spectral resolution to detect meaningful changes in fluorescence. In many methods which monitor fluorescence quenching a small amount of hybridization produces only a small decrease in fluorescence which must be detected in the presence of high levels of background. These methods also suffer from lack of detection sensitivity.

Aptamers are DNA or RNA molecules which bind specific molecular targets. Large populations of randomly generated oligonucleotides may be enriched in aptamers by known in vitro selection and amplification processes. Of particular interest is a single-stranded DNA aptamer which binds thrombin (L. C. Bock, et al. 1992. *Nature* 355:564–566). These thrombin binding aptamers were found to contain the conserved consensus sequence GGNTGGN$_{2-5}$GGNTGG (SEQ ID NO: 1) and inhibited thrombin-catalyzed fibrin-clot formation. Analysis of the structure of this molecule has revealed a symmetrical structure containing two tetrads of guanosine base pairs connected by three loops (1993. K. Y. Wang, et al. *Biochemistry* 32:1899–1904; 1993. R. F. Macaya, et al. *PNAS* 90:3745–3749; 1994. P. Schultze, et al. *J. Mol. Biol.* 235:1532–1547; 1996. J. A. Kelly, et al. *J. Mol. Biol.* 256:417–422). This characteristic structure is commonly referred to as a "G-quartet," "G-quadruplex" or "G-tetraplex" structures. E. Dias, et al. (1994. *J. Am. Chem. Soc.* 116:4479–4480) report a similar sequence in which the G-quartet structure is maintained when the length of the oligonucleotide between the G pairs is increased.

A fluorophore is a dye or chemical moiety which can be made to fluoresce. This includes dyes which fluoresce in response to chemical treatment, excitation by light or in biological systems.

A donor or donor fluorophore is a fluorophore which has a fluorescence emission spectrum which overlaps the absorption spectrum of the second dye or chemical moiety.

An acceptor or acceptor dye is a dye or other chemical moiety which absorbs light emitted by a donor fluorophore.

SUMMARY OF THE INVENTION

It has now been found that oligonucleotides which form G-quartet structures are useful for detection or identification of nucleotide sequences using measurable changes in fluorescence resulting from a change in the distance between two dye labels linked to the G-quartet oligonucleotide (e.g., energy transfer or fluorescence quenching) When the G-quartet oligonucleotide is labeled with a donor fluorophore and an appropriate acceptor dye, the characteristic structure of the G-quartet brings the donor-acceptor pair into close proximity, resulting in an interaction between the labels which results in quenching of donor fluorescence. Upon hybridization to a complementary oligonucleotide the G-quartet structure unfolds or linearizes. This increases the distance between the two dye labels, resulting in a decrease in their interaction and a decrease in fluorescence quenching (i.e., an increase in donor fluorescence) which may be monitored as an indication of the presence of a selected nucleic acid sequence. If the acceptor dye is also a fluorophore, it may in some cases exhibit a decrease in fluorescence as the G-quartet linearizes and the distance between the donor and acceptor increases. If so, the decrease in fluorescence of the acceptor may also be measured as an indication of the presence of the selected nucleic acid sequence. Similar structures, such as i-tetraplexes, may have similar utility.

DESCRIPTION OF THE DRAWING

FIG. 1 shows the results of Example 2.

FIG. 2 shows the results of Example 3.

FIG. 3 shows the results of Example 4.

FIG. 6 shows the results of Example 5.

DETAILED DESCRIPTION OF THE INVENTION

G-quartet oligonucleotide structures, when labeled with a donor fluorophore and an acceptor dye, provide detector molecules or labels in which fluorescence quenching is unexpectedly efficient. In addition, it was unexpectedly found that the G-quartet structure was rapidly disrupted in the presence of the complementary sequence despite its high stability under normal laboratory conditions. Disruption of the G-quartet structure by unfolding or linearizing is a highly specific indicator of hybridization of the G-quartet oligonucleotide to its complement, as in the absence of the complementary sequence no unfolding or disruption of the structure occurs and fluorescence remains efficiently quenched.

G-quartet oligonucleotides according to one embodiment of the invention comprise the sequence $GGN_xGGN_yGGN_zGG$ (SEQ ID NO:2), wherein x, y and z indicate a variable number of nucleotides N. While x, y and z are each typically at least about 2, preferably about 2–10, these segments may be longer if desired, as they do not effect the proximity of the 5' and 3' end in the folded G-quartet structure, as described below. The G-quartet structure brings the 5' and 3' ends, as well as internal segments of the linear sequence of the oligonucleotide, into close proximity. For many donor and acceptor dye pairs the distance between the dyes in the G-quartet is less than the Förster distance or otherwise sufficiently close to allow dye-dye interactions which affect the fluorescence intensity of one or both. The relative position of the 5' and 3' ends and internal segments of the oligonucleotide in the G-quartet structure is therefore the essential feature for using G-quartet oligonucleotides as detector molecules or labels in fluorescence quenching assays, and this proximity is related to the four pairs of G's which are invariant in the oligonucleotide sequence. The regions of variable sequence (i.e., $N_x$, $N_y$, $N_z$) are not critical in the present invention and may be varied in length and sequence without disrupting the characteristic G-quartet structure which gives these molecules their utility in the inventive assays. As a general rule, the variable N sequences should not be self-complementary and should not contain G residues which would result in alternative G-quartet structures within the molecule. Representative G-quartet oligonucleotides according to the invention, 15–20 nucleotides in length, are shown in the Examples, but G-quartet oligonucleotides of any length which conform to the general formula of SEQ ID NO:2 are also suitable. This G-quartet oligonucleotide is typically about 14–30 nucleotides in length.

Figure 5A:
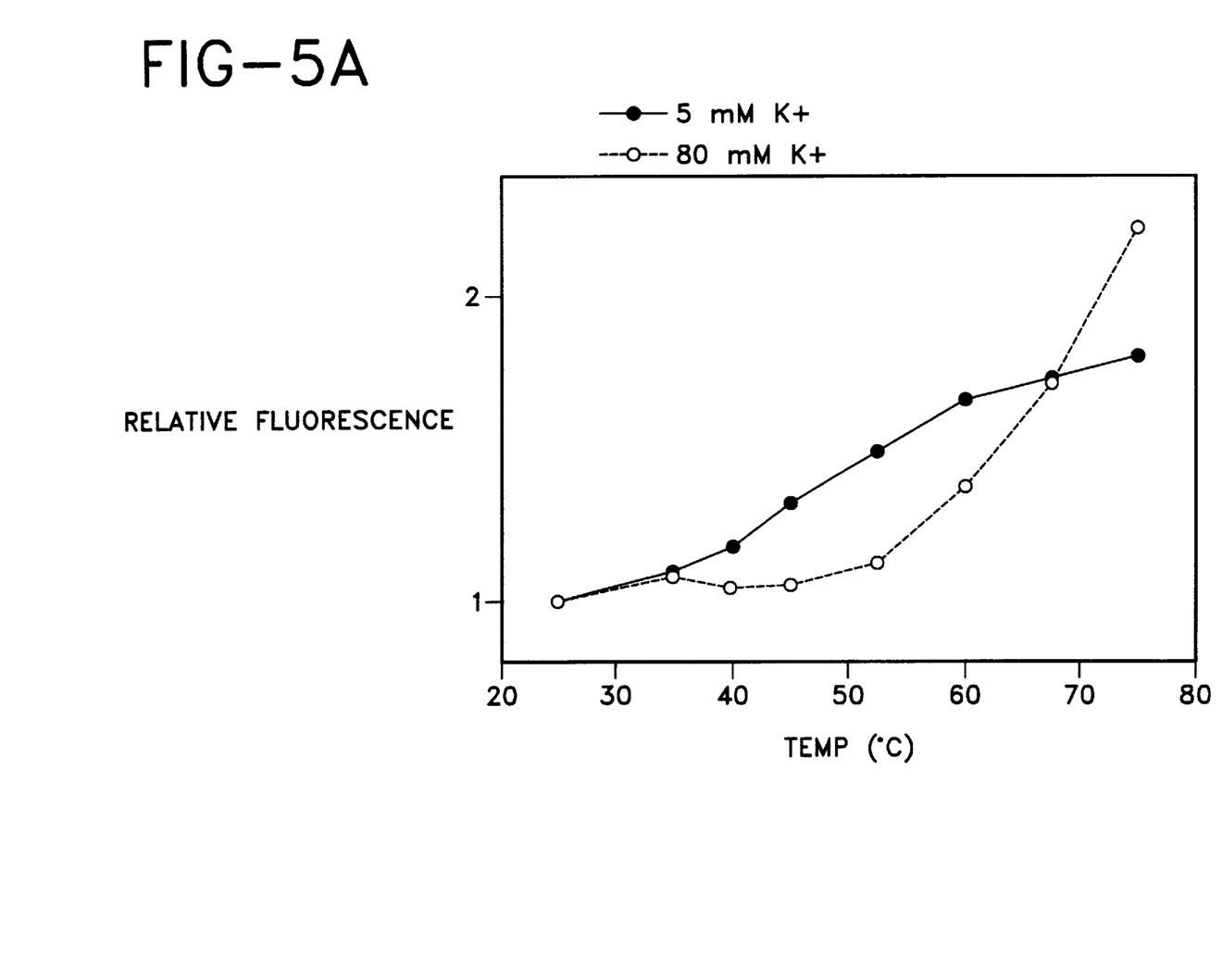
FIG. 5A and FIG. 5B are graphs showing the temperature stability of a two-tetrad G-quartet oligonucleotide (FIG. 5A) and a three-tetrad G-quartet oligonucleotide (FIG. 5B).
Figure 5B:
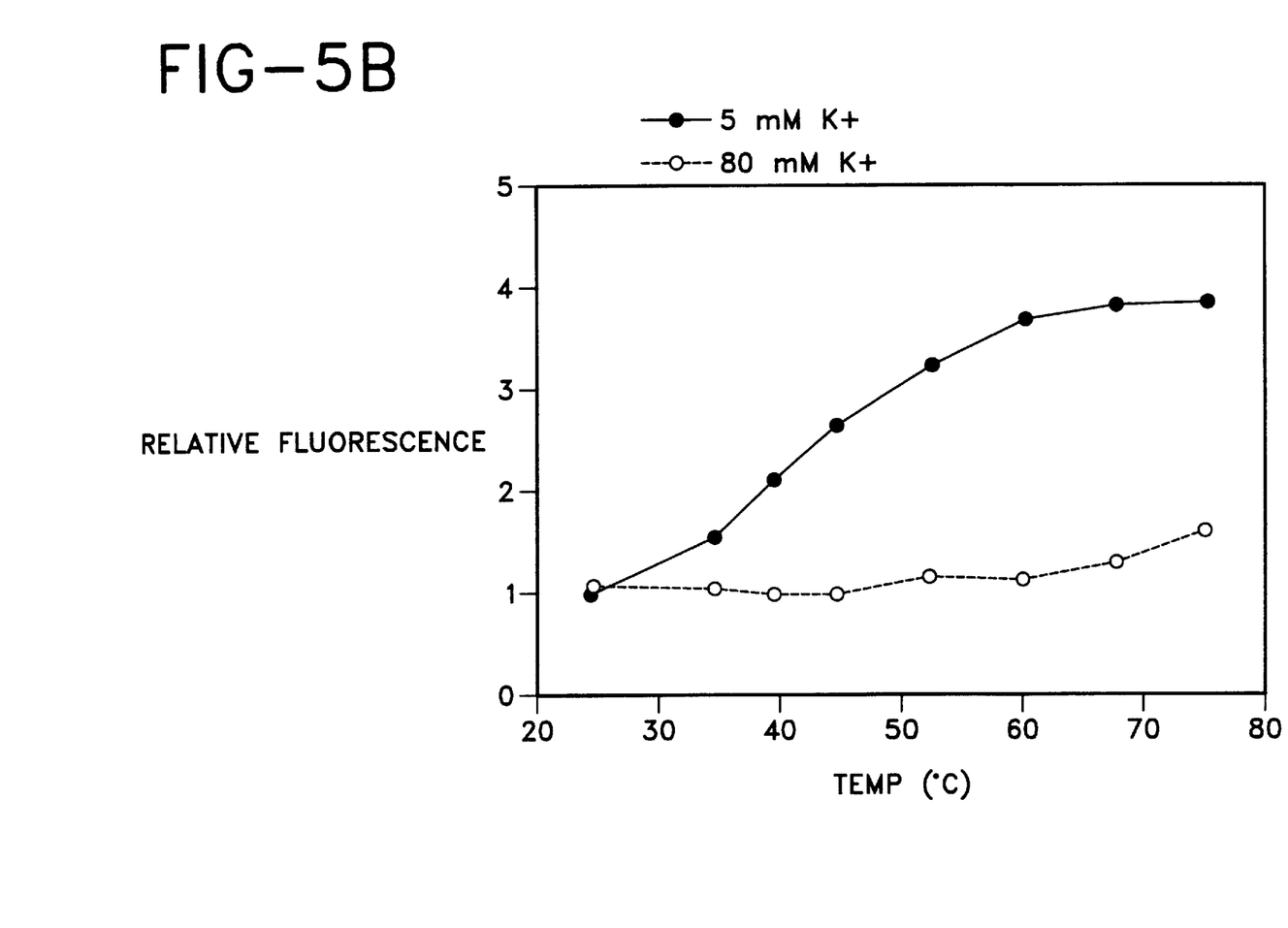

G-quartet oligonucleotides according SEQ ID NO:2 comprise two G-tetrads, each tetrad comprising four of the eight G residues of the oligonucleotide. In a second embodiment of the G-quartet oligonucleotides of the invention, the oligonucleotide comprises twelve G residues and comprises the sequence $GGGN_xGGGN_yGGGN_zGGG$ (SEQ ID NO:9). N, x, y and z are defined as set forth above. A G-quartet sequence according to this formula has been found in human telomeric repeats as reported by Wang and Patel (1993. *Structure* 1:263–282). NMR studies suggest that this oligonucleotide forms three G-tetrads, each comprising four of the twelve G residues. Triple-G-tetrad and quadruple-G-tetrad G-quartet structures are reported by Rhodes and Giraldo (1995. *Cur. Opinions Struct. Biol.* 5:311–322). G-quartet structures comprising three or more G-tetrads have been found to overcome a limitation of G-quartet structures comprising two G-tetrads in that they are more stable at increased temperature but still allow relatively rapid and efficient unfolding in the presence of target. As shown in FIG. 5A, G-quartet oligonucleotides according to SEQ ID NO:2 more rapidly exhibit increases in initial fluorescence as the temperature is increased, most likely due to partial unfolding of the secondary structure. This decreases the overall sensitivity and dynamic range of assays employing SEQ ID NO:2 for detection or identification of nucleic acids at increased temperatures. It is often desirable to perform such assays at elevated temperatures to improve hybridization specificity or increase the rate of an enzymatic reaction such as nucleic acid amplification. By adding additional tetrads to the G-quartet oligonucleotide, the stability of the folded structure at higher temperatures is improved (FIG. 5B) and the number of nucleotides separating the two dye labels in the linear molecule is also increased. That is, in the unfolded, linearized or disrupted 3-tetrad G-quartet structure the two dyes are separated by a greater distance than in the unfolded, linearized or disrupted 2-tetrad G-quartet structure, often providing a greater fluorescence change in the presence of the complementary sequence and improved assay sensitivity.

Hybridization of SEQ ID NO:9 (with $N_x$, $N_y$ and $N_z$ each "TTTT") to its complementary sequence demonstrated improved dynamic range as compared to double G-quartet oligonucleotides. Titration with 0, 0.5, 1.0 and 5.0 molar equivalents of the sequence complementary to SEQ ID NO:9 showed an approximately 6 to 7-fold increase in fluorescence in the presence of 0.5 equivalents of complement, an approximately 12 to 13-fold increase in the presence of 1.0 equivalent of complement and an approximately 17-fold increase in the presence of 5.0 equivalents of complement. Increasing the concentration of potassium reduced sensitivity slightly, with an approximately 3 to 4-fold increase in fluorescence in the presence of 0.5 equivalents of complement, an approximately 6-fold increase in the presence of 1.0 equivalents of complement and an approximately 14-fold increase in the presence of 5.0 equivalents of complement. Potassium and magnesium concentration has been found to affect folding and may be routinely adjusted to optimize assay sensitivity as necessary. In comparison, G-quartet structures containing two G-tetrads typically exhibit a maximum fluorescence increase of about 9-fold in the presence of the complement.

It will be apparent to one skilled in the art that the temperature stability of the G-quartet oligonucleotide may be further improved by adding additional G-tetrads to the structure. This is accomplished by adding additional consecutive G residues to the G domains of SEQ ID NO:9. However, as additional G-tetrads are added to the G-quartet structure it may become so stable that it is not unfolded, linearized or disrupted efficiently in the assay and detection sensitivity may begin to decrease. Applicants believe that a G-quartet oligonucleotide comprising about three to five consecutive G residues in each of the four G domains (forming three to five G-tetrads in the G-quartet structure) will provide sufficient stability for minimal background in fluorescence assays at increased temperatures without significantly compromising assay sensitivity in the unfolding or linearizing portion of the reaction. That is, G-quartet oligonucleotides useful in the assay methods of the invention comprise four G domains, each domain having an equal number of consecutive G residues Each such G domain consists of about two to five consecutive G residues ($G_{2-5}N_xG_{2-5}N_yG_{2-5}N_zG_{2-5}$), resulting in two to five G-tetrads in the G-quartet structure. G-quartet oligonucleotides which exhibit improved performance as detector probes at increased temperatures have the sequence $G_{3-5}N_xG_{3-5}N_yG_{3-5}N_zG_{3-5}$, wherein each of the four G domains has an equal number of consecutive G residues and each such G domain consists of about 3–5 consecutive G residues, resulting in three to five G-tetrads in the G-quartet structure.

The G-quartet oligonucleotide sequences described above form monomeric, intramolecular G-quartet structures (i.e., a single folded oligonucleotide is involved in the structure). However, G-quartet structures according to the invention may also be dimeric or tetrameric, as illustrated by Rhodes and Giraldo, supra. Dimeric G-quartet structures comprise two antiparallel oligonucleotide strands, the first comprising the sequence $G_{2-5}N_xG_{2-5}$ and the second comprising the sequence $G_{2-5}N_yG_{2-5}$. N, x and y are as previously defined, and the G domains of the two oligonucleotides have an equal number of consecutive G residues. Tetrameric G-quartet structures comprise four parallel oligonucleotide strands, each strand comprising 2–5 consecutive G residues.

C-rich oligonucleotides form folded structures similar to the G-quartet. These are typically referred to as i-tetraplexes (Rhodes and Giraldo, supra). These structures are stabilized by intercalation of cytosine residues in a first base-paired duplex between cytosine residues of a second base-paired duplex, the duplexes being in antiparallel orientation in the i-tetraplex. As i-tetraplexes have structural characteristics similar to G-quartets, they are believed to be readily substituted for G-quartets in the methods of the present invention when labeled as described herein.

Monitoring the unfolding, linearizing or disruption of a G-quartet structure labeled with a donor and acceptor dye pair has several advantages over monitoring linearization of similarly labeled self-complementary oligonucleotides of the prior art. First, as the G-quartet is not self-complementary, it unfolds or is disrupted more readily in the presence of the complementary oligonucleotide, providing a more rapid change in fluorescence and a more rapid assay result. Further, multiple G-quartet structures may be incorporated into a single oligonucleotide to amplify the fluorescent signal and enhance the change in fluorescence intensity in the presence of a complementary sequence. In such multimedia G-quartet structures the ratio of acceptor to donor fluorophore may be increased to improve donor quenching, thereby providing a greater change in fluorescence intensity in the presence of the complementary sequence.

Optionally, the donor and acceptor may flank a restriction endonuclease recognition site (RERS) in an oligonucleotide comprising a G-quartet structure. That is, an RERS may be present in the G-quartet-forming sequence of the oligonucleotide at a position between the donor and acceptor dye. Inclusion of an RERS provides the advantage of permanent conversion of the G-quartet oligonucleotide into a structural form which exhibits altered fluorescence, i.e., cleavage or nicking prevents reassociation of the G-quartet oligonucleotide into the quenched structure. In this embodiment, the characteristic folding of the G-quartet structure brings the dyes into close spatial proximity while the RERS remains partially or entirely single-stranded in a single-stranded portion of the G-quartet structure between the two dyes, typically in a single-stranded loop of a monomeric or dimeric G-quartet. In the G-quartet oligonucleotide, the RERS sequence corresponds to one strand of the double-stranded RERS. Either the donor or acceptor dye is linked to the G-quartet oligonucleotide 3' to the RERS. The donor fluorophore (if the acceptor is 3' to the RERS) or the acceptor (if the donor is 3' to the RERS) is linked to the G-quartet oligonucleotide at a position 5' to the RERS. That is, the donor and acceptor dyes flank the RERS. The dyes are preferably linked on either side of the RERS at positions sufficiently far apart to allow the restriction endonuclease access to the RERS for cleavage or nicking.

Many donor/acceptor dye pairs known in the art are useful in the present invention. These include, for example, fluorescein isothiocyanate (FITC)/tetramethylrhodamine isothiocyanate (TRITC), FITC/Texas Red™ Molecular Probes), FITC/N-hydroxysuccinimidyl 1-pyrenebutyrate (PYB), FITC/eosin isothiocyanate (EITC), N-hydroxysucciniridyl 1- pyrenesulfonate (PYS)/FITC, FITC/Rhodamine X (ROX), FITC/tetramethylrhodamine (TAMRA) and others. The selection of a particular donor/acceptor pair is not critical. It is only necessary that the emission wavelengths of the donor fluorophore overlap the absorption wavelengths of the acceptor, i.e., there must be sufficient spectral overlap between the donor and acceptor to allow fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Certain donor/acceptor pairs are exemplified above and in the following Examples, however, others will be apparent to those skilled in the art and are also useful in the invention. Fluorescein and ROX or ROX and Cy5 are preferred donor/acceptor dye pairs for use in the invention.

The donor and acceptor are terminally or internally linked to the oligonucleotide comprising the G-quartet structure such that fluorescence quenching occurs in the G-quartet structure and quenching is decreased when the G-quartet structure is unfolded, linearized or disrupted in the presence of target. They may be linked to any site in the oligonucleotide which produces this result, which is due to increased distance between the donor and the acceptor in the unfolded, linearized, or disrupted structure Preferably, at least one of the dyes (either the donor or the acceptor) is linked within the sequence involved in forming the G-quartet structure. The second dye may also be linked within the sequence which forms the G-quartet structure at a position which will be at an increased distance when the G-quartet structure is disrupted. Alternatively, the second dye may be linked to a single-stranded sequence in the oligonucleotide which is not involved in G-quartet formation, for example, a single-stranded target binding sequence as described below.

5'-terminal labeling and 3'-terminal labeling methods are also known in the art and may be used to link the donor and acceptor dyes to their respective ends of the G-quartet oligonucleotide. For example, 3'-terminal labeling methods include a) periodate oxidation of a 3'-terminal ribonucleotide followed by reaction with an amine-containing label, b) enzymatic addition of a 3'-aliphatic amine-containing nucleotide using terminal deoxynucleotidyl transferase followed by reaction with an amine-reactive label, and c) periodate oxidation of a 3'-ribonucleotide followed by reaction with 1,6-hexanediamine to provide a 3'-terminal aliphatic amine which can be reacted with an amine-reactive label. Examples of 5'-terminal labeling methods include a) periodate oxidation of a 5'-to-5'-coupled ribonucleotide followed by reaction with an amine-containing label, b) condensation of ethylenediamine with a 5'-phosphorylated polynucleotide followed by reaction with an amine-reactive label, and c) introduction of an aliphatic amine substituent using an aminohexyl phosphite reagent in solid-phase DNA synthesis followed by reaction with an amine-reactive label. Labels may also be linked to synthetic DNA oligonucleotides at specific interior or terminal locations using special aliphatic amine-containing nucleotide phosphoramidite reagents. Selection of an appropriate method for linking the selected labels to the G-quartet oligonucleotide and performing the linking reactions are routine in the art. It is also to be understood that the present description of labels at the 5' and 3' ends of a G-quartet structure is intended to include labels which are near the ends, i.e., not linked to the terminal nucleotides but close enough to the ends that quenching occurs in the G-quartet structure. Linkage of the donor and acceptor is typically within about 2–4 nucleotides of the terminal nucleotide. Only routine testing is required to determine what donor/acceptor pair linkages near the 5' and 3' ends of the G-quartet oligonucleotide provide quenching of donor fluorescence in the folded G-quartet structure. Further, when the G-quartet sequence is contained in or linked to a larger oligonucleotide probe for use as a detector molecule or label (as in Example 3), either the donor or acceptor, or both, may be linked to an internal nucleotide in the probe, preferably at a position which is at or near the end of the sequence which forms the G-quartet structure. These linkages may be to nucleotides which are within the sequence which forms the G-quartet structure or they may be to nucleotides which are at or near the end of the G-quartet sequence in the probe portion of the oligonucleotide (i.e., outside of the G-quartet sequence). Such linkages are all considered to be at or near the end of the G-quartet sequence or structure. Routine testing may be employed to determine which nucleotides at or near the ends of the G-quartet are suitable for linking donor fluorophores and acceptor dyes to achieve donor quenching in such probes.

G-quartet oligonucleotides labeled according to the invention may be used in a variety of assays for detection or identification of selected nucleic acid sequences. The essential feature of such assays is that the G-quartet structure is unfolded, linearized or disrupted in a manner which is dependent upon the presence of the selected nucleic acid sequence. This process results in a detectable increase in donor fluorescence due to decreased quenching. It is not necessary that the donor be totally quenched prior to disruption of the G-quartet, as the assay depends only on a change in donor fluorescence intensity of sufficient magnitude to be detected as an indication of the presence of the selected nucleic acid sequence. While any means which sequence-specifically disrupts the G-quartet structure is useful in the invention, certain examples are provided. Disruption of the structure by unfolding or linearization may be accomplished by hybridization of the G-quartet oligonucleotide to the complement of the G-quartet sequence. If the complement of the G-quartet oligonucleotide is itself the sequence which is to be detected, or if the selected nucleic acid sequence contains the complement of the G-quartet, an increase in donor fluorescence intensity upon hybridization of the labeled G-quartet oligonucleotide may be used to directly detect the selected nucleic acid sequence. If, however, the sequence to be detected does not contain a sequence complementary to the G-quartet other methods must be employed to unfold the G-quartet structure in a sequence-specific manner. For example, the labeled G-quartet oligonucleotide may be linked to the 5'-end of a detector probe which hybridizes to the 3' end of the nucleic acid sequence to be detected or identified such that the G-quartet forms a 5' overhang. Upon hybridization, the selected nucleic acid sequence and the detector probe are made double-stranded by a polymerase using the hybridized segment of the selected nucleic acid sequence as a priming site. Extension of the selected nucleic acid sequence using the detector probe with the G-quartet as a template causes the G-quartet structure to unfold and linearize as the complementary sequence is synthesized through this segment of the detector probe. The resulting increase in donor fluorescence indicates the presence of the sequence to which the detector probe hybridizes. Alternatively, the labeled G-quartet oligonucleotide may be linked to the 5' end of a signal primer as described in published European Patent Application 0 678 582. Following hybridization of the signal primer to the selected nucleotide sequence, extension and displacement produce a single-stranded secondary amplification product which comprises the G-quartet structure at the 5' end. This secondary amplification product hybridizes to a second amplification primer and extension of the hybridized second amplification primer by polymerase renders the secondary amplification product, including the G-quartet, double-stranded. That is, as the complement of the secondary amplification product is synthesized through the region of the linked G-quartet structure, the G-quartet is unfolded and the distance between the two labels is increased. Enhanced fluorescence intensity of the donor fluorophore indicates the presence of double stranded secondary amplification products and the presence of the selected nucleic acid sequence (i.e., the target sequence being amplified). Of course, in any of the inventive assays a decrease in fluorescence of an acceptor fluorophore may be monitored as an indication of the presence of the selected nucleic acid sequence instead of an increase in donor fluorescence if the acceptor is a fluorophore which responds to increased distance from the donor in this manner.

Unfolding or disruption of the G-quartet structure according to the invention may also be detected or monitored by means of other fluorescence properties which increase or decrease as the proximity of donor and acceptor changes. For example, quenching of the donor decreases its fluorescence intensity but may also produce a decrease in its fluorescence lifetime (i.e., the time between excitation and emission). As fluorescence intensity of the donor increases in the unfolded G-quartet, donor fluorescence lifetime may also increase and be detected as an alternative to detecting decreased donor quenching (increased fluorescence intensity). Similarly, fluorescence polarization may change as the distance between the two dyes changes. The change in molecular volume associated with conversion of the G-quartet oligonucleotide from single-stranded to double-stranded form contributes to changes in fluorescence polarization, but fluorescence polarization may also be influenced by the change in proximity of the two dyes. Changes in fluorescence polarization or anisotropy may therefore also be a useful alternative for monitoring or detecting disruption of the G-quartet.

EXAMPLE 1

Fifteen-mer (GGTTGGTGTGGTTGG, SEQ ID NO:3) and 20-mer (GGTTTTGGTTTTGGTTTTGG, SEQ ID NO:4) G-quartet oligonucleotides and their complements were synthesized by conventional methods. Measurements of the circular dichroism (CD) spectra for the 15-mer and the 20-mer were very similar and differed considerably from both double-stranded and single-stranded DNAs of comparable length which do not assume the G-quartet structure (L. B. McGown, et al. Nov. 1, 1995. *Anal. Chem.* pgs. 663A–668A) This confirmed that both oligonucleotides fold efficiently into G-quartets. The oligonucleotides were labeled at the 5' end with fluorescein (the donor) and at the 3' end with either tetramethyfrhodamine (TAMRA) or rhodamine-X (ROX). G-quartet oligonucleotides labeled only at either the 5' or 3' end with fluorescein served as unquenched controls. The 5' fluorescein was attached during oligonucleotide synthesis using the 6-FAM reagent (ABI). At the 3' end, fluorescein was linked by use of a fluorescein derivative immobilized on CPG column material (Glen Research, Sterling, Va.). Dyes other than fluorescein were linked to the 3' end of the oligonucleotide via their NHS esters to aminoalkyl linkers using a similar CPG strategy. The labeled oligonucleotides were purified by removal of unreacted dye with size exclusion chromatography (NAP-5 column, Pharmacia) and by elution through an OPC cartridge (ABI). The concentrations of the labeled oligonucleotides were derived from the calculated absorbance at 260 nm corrected for the dye absorbance at the same wavelength. The fluorescence spectra were analyzed using either an SLM-Aminco 8100 research grade spectrofluorometer or an FPM-1 fluorometer (Jolley Consulting) equipped with filters for fluorescein excitation and emission.

The dye labeled oligonucleotide (2–10 nM) was added to a buffer consisting of 20 mM TRIS acetate, 140 mM NaCl, 5 mM KCl, 1 mM $CaCl_2$, and 1 mM $MgCl_2$ at pH 7.5 at ambient temperature (about 24°–26° C.). The complementary sequence was added in a 1.5-fold or greater molar excess and final measurements were taken when no further changes were seen in the fluorescence spectrum. This typically took less than 30 min. The donor intensity change was determined at the emission wavelength of fluorescein (about 520 nm) with excitation at 485 or 488 nm. The percent quenching was determined by comparison to a similar sequence labeled only with fluorescein at the 5' end. The results are shown in the following Table:

| APTAMER LENGTH | 5'-DONOR DYE | 3'-ACCEPTOR DYE | QUENCHING (%) | INTENSITY INCREASE (Donor Emission) |
|---|---|---|---|---|
| 15-mer | Fluorescein | Rhodamine-X | 25 | 9X |
| 15-mer | Fluorescein | TAMRA | 60 | 5X |
| 15-mer | Fluorescein | Fluorescein | NA | 2.5X |
| 20-mer | Fluorescein | TAMRA | 30 | 2.4X |
| 20-mer | Fluorescein | Fluorescein | NA | 1.7X |

Upon hybridization, readily detectable increases in the intensity of fluorescein fluorescence were observed for all donor/acceptor dye pairs and both oligonucleotides upon hybridization. The fluorescein donor and rhodamine-X acceptor on the 15-mer resulted in the largest increase (9-fold), but the expected decrease in the acceptor (ROX) emission was smaller than predicted (less than 2-fold). This suggests that some of the fluorescence quenching may be due to mechanisms other than Förster energy transfer. The results reported in the Table above show the increase in the emission of the donor. However, with sufficient change, a decrease in the emission of the acceptor could also be used to monitor disruption of the G-quartet upon hybridization. This would give a large effective Stokes shift, as excitation would be at the donor wavelength but emission would be monitored at the wavelength of the acceptor. This configuration would also result in less interference from sample background.

Changes in fluorescence polarization upon hybridization of SEQ ID NO:3 (5' fluorescein, 3' TAMRA) were also monitored under similar experimental conditions. With donor excitation at 475 nm and emission monitored at 585 nm fluorescence polarization increased from 62 to 138 mP upon hybridization of the complement.

EXAMPLE 2

Figure 1:
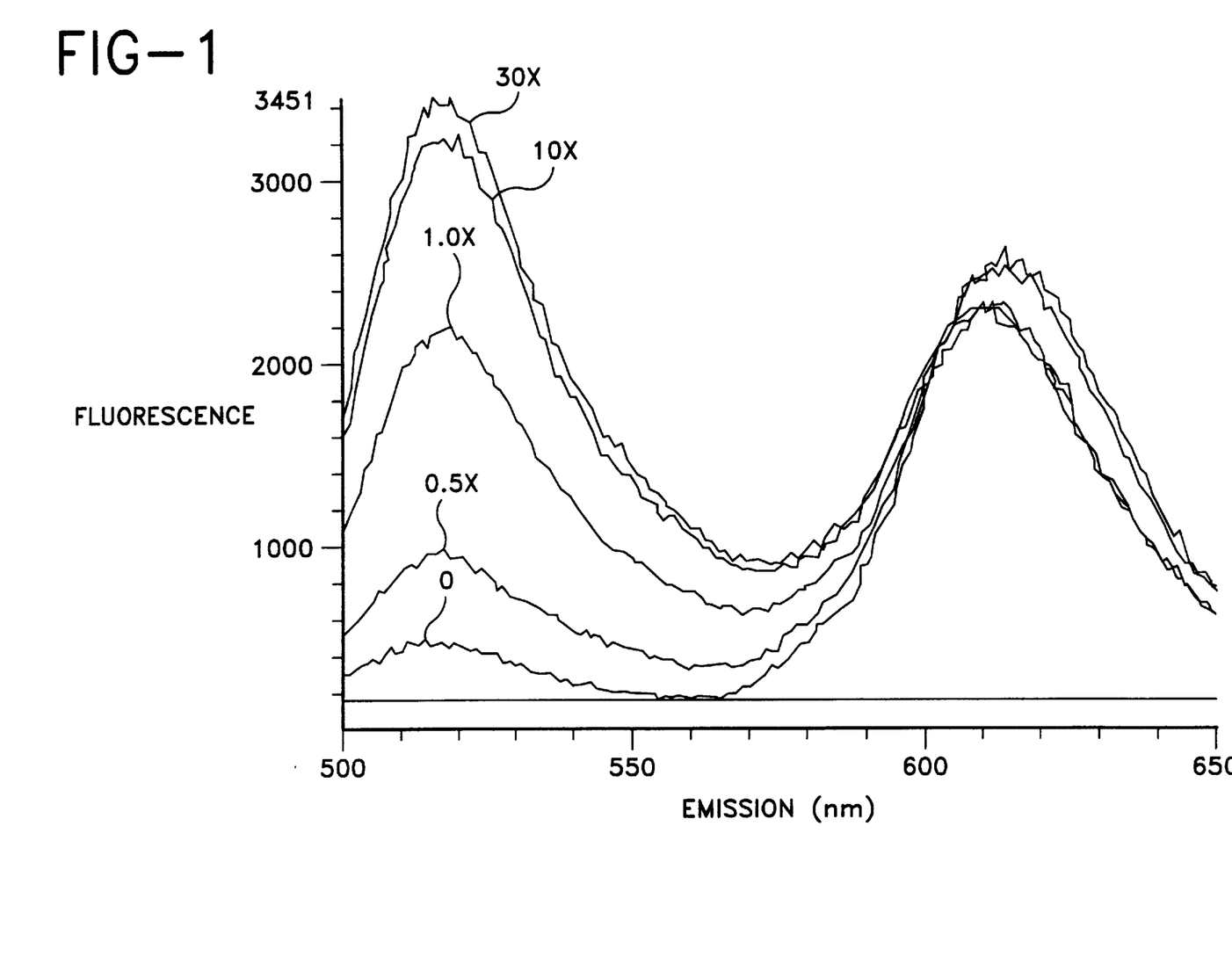
FIG. 1 is a graph illustrating the increase in donor fluorescence observed when a two-tetrad G-quartet structure hybridizes to its complementary sequence.

In an experiment similar to Example 1, increasing amounts of the 15-mer complementary oligonucleotide were added to SEQ ID NO:3 labeled at the 5' end with fluorescein and at the 3' end with ROX. The complementary sequence was added at 0.5 molar equivalents, 1.0 molar equivalent, 10 molar equivalents and 30 molar equivalents of SEQ ID NO:3. The absence of the complementary oligonucleotide provided baseline fluorescence readings. After addition of the complementary oligonucleotide the samples were incubated at room temperature for five minutes. The dyes were excited at 485 nm and the emission spectra were recorded. The results are shown in FIG. 1. Emission at 520 nm increased with increasing amounts of the complement: 2-fold (0.5 equivalents), 5-fold (1.0 equivalents), 8-fold (10 equivalents) and 9-fold (30 equivalents). Unfolding of more G-quartets and greater reductions in quenching therefore occur as more of the complementary oligonucleotide hybridizes. This suggests that the method may be semiquantitative, or possibly quantitative, and useful as a means for estimating the amount of a selected nucleotide sequence present in a sample or for comparing relative quantities of the selected sequence in different samples.

EXAMPLE 3

A G-quartet sequence was added to the 5' end of a probe for detection of Chlamydia organisms. The sequence was labeled with 6-FAM at the 5' end and with ROX at T-16 as follows (SEQ ID NO:5):

F-GGTTGGTGTGGTTGGT*CTAGAGTCTTCAAATATCAGAG CTTTACCTAACAA

F=fluorescein
T*=dT with amino-C6 linker to ROX (Rhodamine X)

The probe was synthesized on an ABI 380B synthesizer with ABI's 6-FAM reagent and the dT C6 amino linker from Glen Research was inserted at the indicated position. Following deprotection the crude oligonucleotide was purified by reverse phase HPLC using a Waters C18 Delta Pak 300 Å C18 3.9×150 mm column using a linear solvent gradient from 2% to 30% acetonitrile in 50 mM TEAA over 30 min. Half of this (0.5 μmole) was dissolved in 100 μL of 100 mM sodium carbonate/bicarbonate buffer at pH 8 and 30 μL of a DMSO solution of 5 mg/60 μL ROX NHS ester (ABI/Perkin Elmer) was added. The resulting mixture was allowed to stand in the dark for 24 hr. at 37° C. and was passed over a column of G-25 SEPHADEX Resin (NAP5, Pharmacia Biotech) eluting with 4 mM TAE (4 mM TRIS acetate, 0.1 mM EDTA, pH 8.0). This product was purified by HPLC as described above. An unlabeled oligonucleotide (SEQ ID NO:6) was synthesized by conventional methods to serve as a target for hybridization of SEQ ID NO:5 and as a primer for extension using SEQ ID NO:5 as a template. This oligonucleotide (TTGTTAGGTAAAGCTCTGATATTTGAAG) was complementary to the 3' end of the probe.

Four 100 μL cuvettes containing 20 nM fluorescent probe, 40 mM KiPO$_4$, 5 mM Mg(OAc)$_2$, 0.2 mM each deoxynucleoside triphosphate, 1.4 mM alpha-thio-dCTP, 5% glycerol and either 0, 0.2, 1.0 or 10 equivalents of target oligonucleotide were prepared and placed in an SLM 8100 fluorometer with the sample chamber preheated to 53° C. Bst polymerase (New England BioLabs, 25 U/100 μL) was added to each sample and the fluorescence intensity was measured over time for all four samples. Excitation was at 484 nm (slits at 4 nm/4 nm) and emission was set at 520 nm (slits at 10 nm/10 nm).

Figure 2:
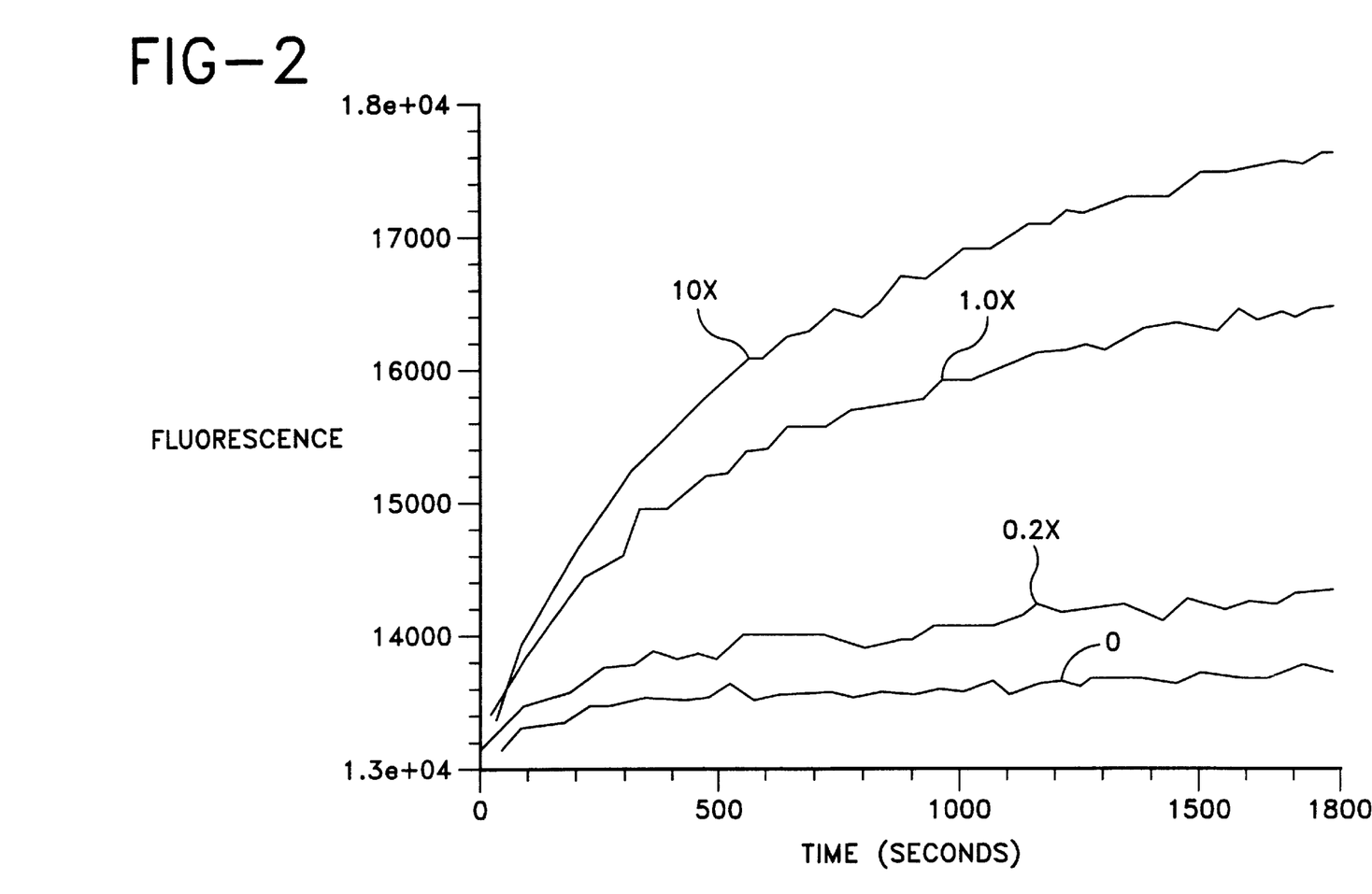
FIG. 2 is a graph illustrating the increase in donor fluorescence when a hybridized primer is extended through a two-tetrad G-quartet structure, thereby unfolding or linearing the G-quartet structure and increasing the distance between the donor fluorophore and the acceptor.

The results are shown in FIG. 2. The increase in donor fluorescence in the presence of target indicates unquenching resulting from an increase in the distance between the two fluorophores as the complement is synthesized and the G-quartet is unfolded and linearized. The magnitude of the change in fluorescence increases with increasing amounts of target, indicating at least a semi-quantitative assay. Further, FIG. 2 illustrates that there is a more rapid rate of increase when more target is present. This indicates utility for real-time detection of nucleic acids using primer extension to disrupt the G-quartet, possibly semi-quantitatively, in SDA reactions or other assays based on extension of a hybridized primer.

EXAMPLE 4

A probe for detection of the IS6110 insertion element of *Mycobacterium tuberculosis* linked to a G-quartet at the 5' end was tested in a primer extension assay similar to Example 3. The detector probe was labeled at the 5' end with 6-FAM and with TAMRA at T-16 as follows (SEQ ID NO:7):

F-GGTTGGTGTGGTTGGT*TTATCCGTATGGTGGATAACG TCTTTCA

F=fluorescein
T*=dT linked to TAMRA

Figure 3:
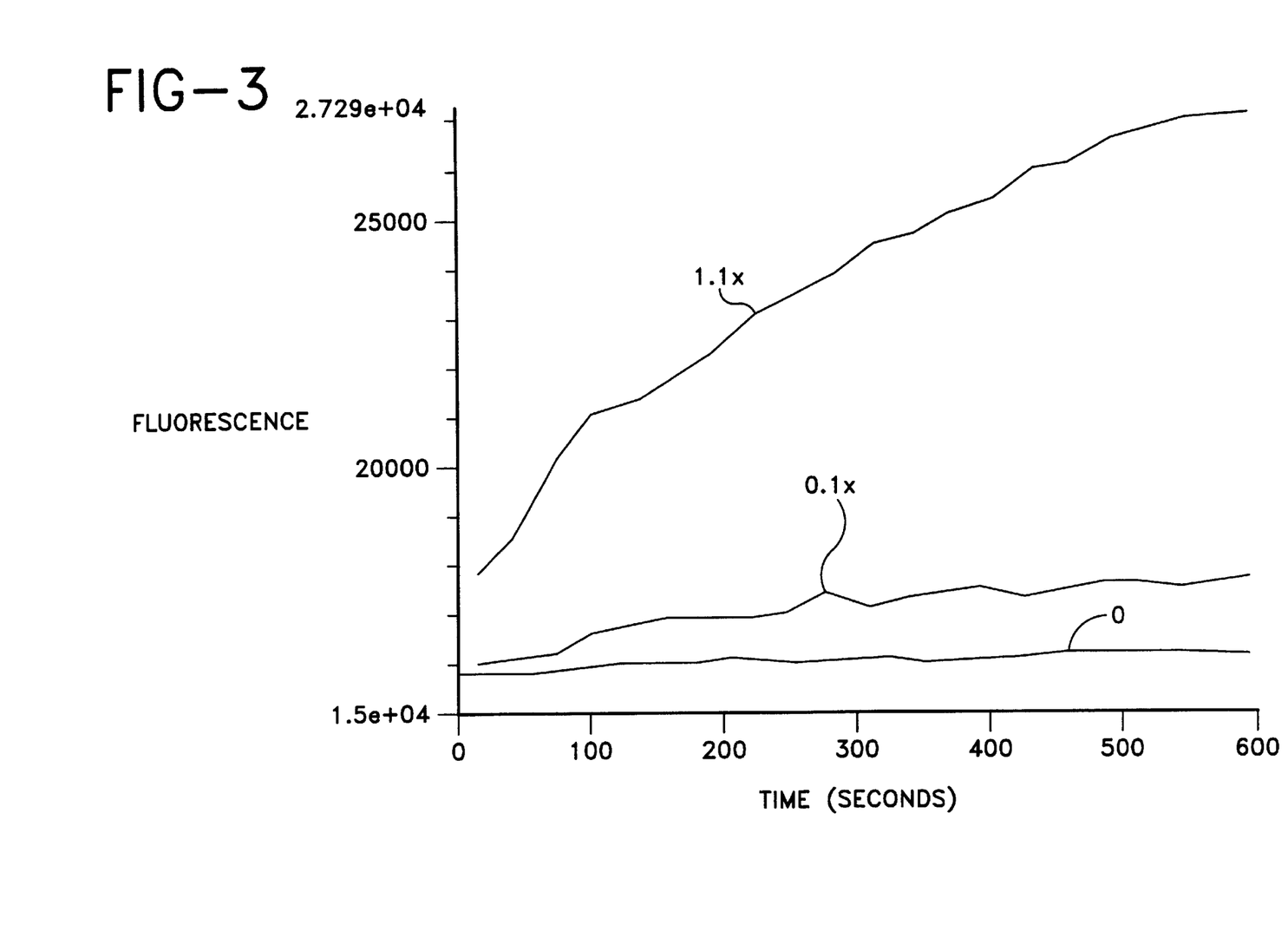
FIG. 3 is also a graph illustrating the increase in donor fluorescence when a hybridized primer is extended through a two-tetrad G-quartet structure.

The oligonucleotide complementary to the 3' end of the detector probe was SEQ ID NO:8 (GACGTTATCCACCATACGG). The experiment was performed at 55° C. as in Example 3, with 0, 0.1 and 1.1 equivalents of SEQ ID NO:8 present. FIG. 3 shows an increase in donor fluorescence in the presence of target. This is due to the increased distance between the donor and acceptor of the detector probe as the complementary sequence is synthesized using the hybridized target oligonucleotide as a primer. The greater the amount of target present, the greater the magnitude of the increase in fluorescence. Again, a more rapid rate of increase in fluorescence was observed when more target was present. In this experiment the magnitude of the change in fluorescence with a ten-fold increase in target was significantly larger than in Example 3, suggesting that this may be a more sensitive assay system.

Figure 4:
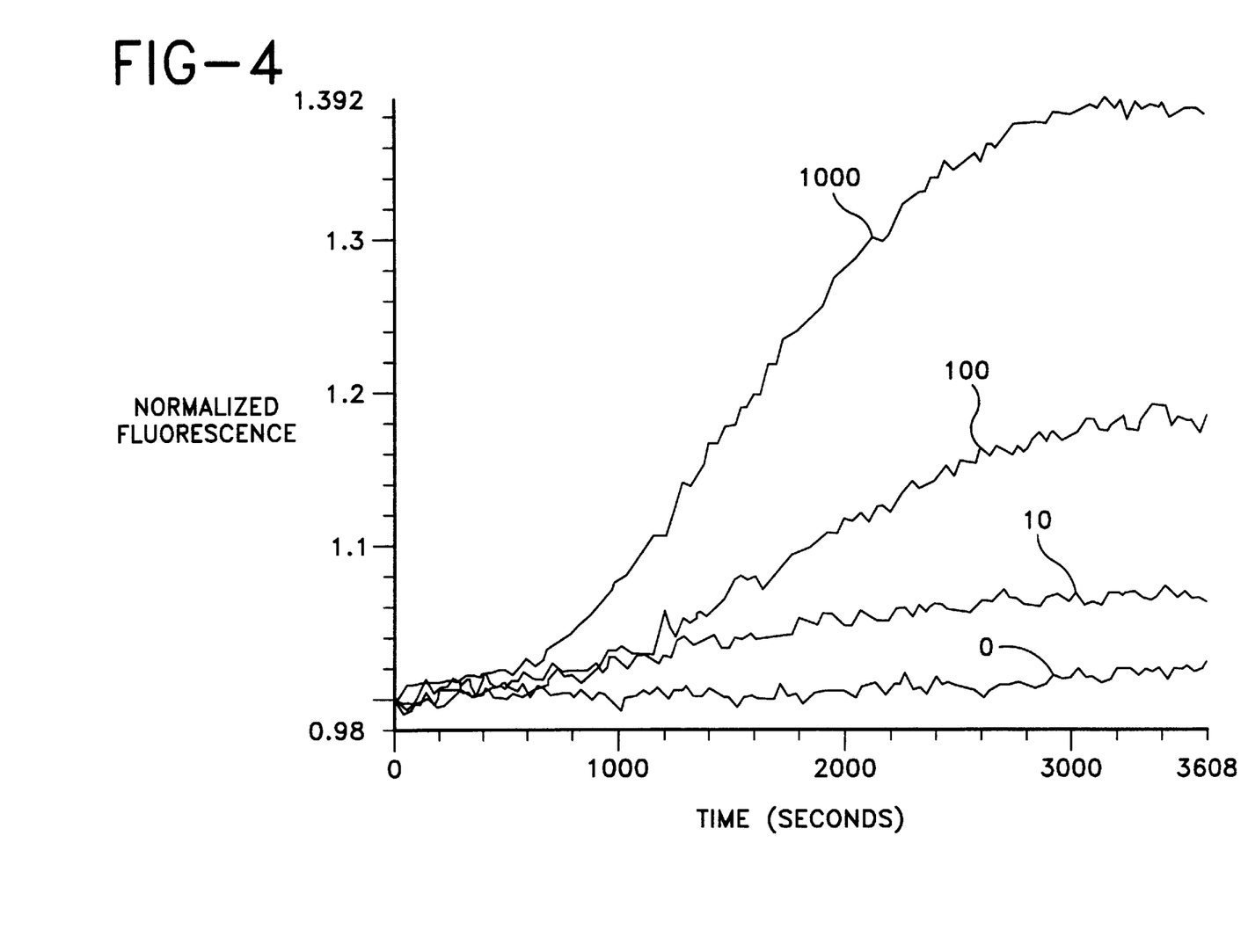
FIG. 4 is a graph illustrating the increase in donor fluorescence when a two-tetrad G-quartet structure, linked to a donor fluorophore and an acceptor dye, is used as a detectable label on a signal primer to detect target amplification in a Strand Displacement Amplification reaction.

Examples 3 and 4 demonstrate the essential feature for use of G-quartets as labels or detector molecules on signal primers in SDA and other amplification reactions, i.e., the ability of an amplification primer to hybridize to a signal primer with a G-quartet at its 5' end and be extended through the G-quartet, thereby disrupting the G-quartet structure and increasing the distance between the donor and acceptor. The decrease in the proximity-dependent interaction between the two labels results in a measurable change in the fluorescence of one or both of the labels. This was demonstrated in an SDA reaction performed generally as described in EP 0 684 315. The amplification reactions were conducted at 55° C., using AvaI as the restriction endonuclease and SEQ ID NO:7 as the signal primer. Genomic DNA of *M. tuberculosis* was added as the target for amplification. The results are shown in FIG. 4. Donor fluorescence remained constant at a low level over time in the control reaction which contained no target. In the amplification reactions containing target (10, 100 or 1000), donor fluorescence increased measurably over time as the target was amplified. These results indicate that the signal primer was extended, displaced and rendered double-stranded as a result of target amplification and that the G-quartet sequence in the signal primer was unfolded as this process occurred. An increase in fluorescence as the G-quartet structure is disrupted in a target amplification-specific manner is therefore a useful method for detecting target amplification. Further, the rate of increase in donor fluorescence intensity is more rapid as the initial amounts of target increases. The rate of increase in donor fluorescence intensity (i.e., the rate of decrease in donor quenching) is therefore at least a semi-quantitative indication of the initial amount of target in the sample and may also be used to compare the relative initial amounts of target contained in multiple samples.

The polymerase extension experiment was repeated using a similar probe comprising a G-quartet structure at the 5' end and a single-stranded target binding sequence at the 3' end, except that the G-quartet structure further comprised a RERS for BsoBI (underlined), as follows (SEQ ID NO:11):

F-GGTTGGCTCGAGGTTGGT*TTATCCGTATGGTGGATAAC
GTCTTTCA

F=fluorescein
T*=dT linked to TAMRA

Upon hybridization and extension of SEQ ID NO:8, followed by cutting with the restriction endonuclease, a 3.4-fold increase in donor fluorescence was observed. The magnitude of the change in fluorescence was larger than that observed for linearization of the G-quartet structure alone.

EXAMPLE 5

A G-quartet structure was added to the 5' end of a probe for detection of Chlamydia organisms. The G-quartet sequence contained three consecutive G residues in each of the four G domains and is believed to form three tetrads in the G-quartet structure. The sequence was labeled with 6-FAM at the 5' end and with ROX at T-25 as follows (SEQ ID NO: 10):

GTATATGGGTAATGGGTATGGGT*GTCTTCAAATATCAG
AGCTTTACCTAACAA

F=fluorescein
T*=dT with amino-C6 linker to ROX (Rhodamine X)

Figure 6:
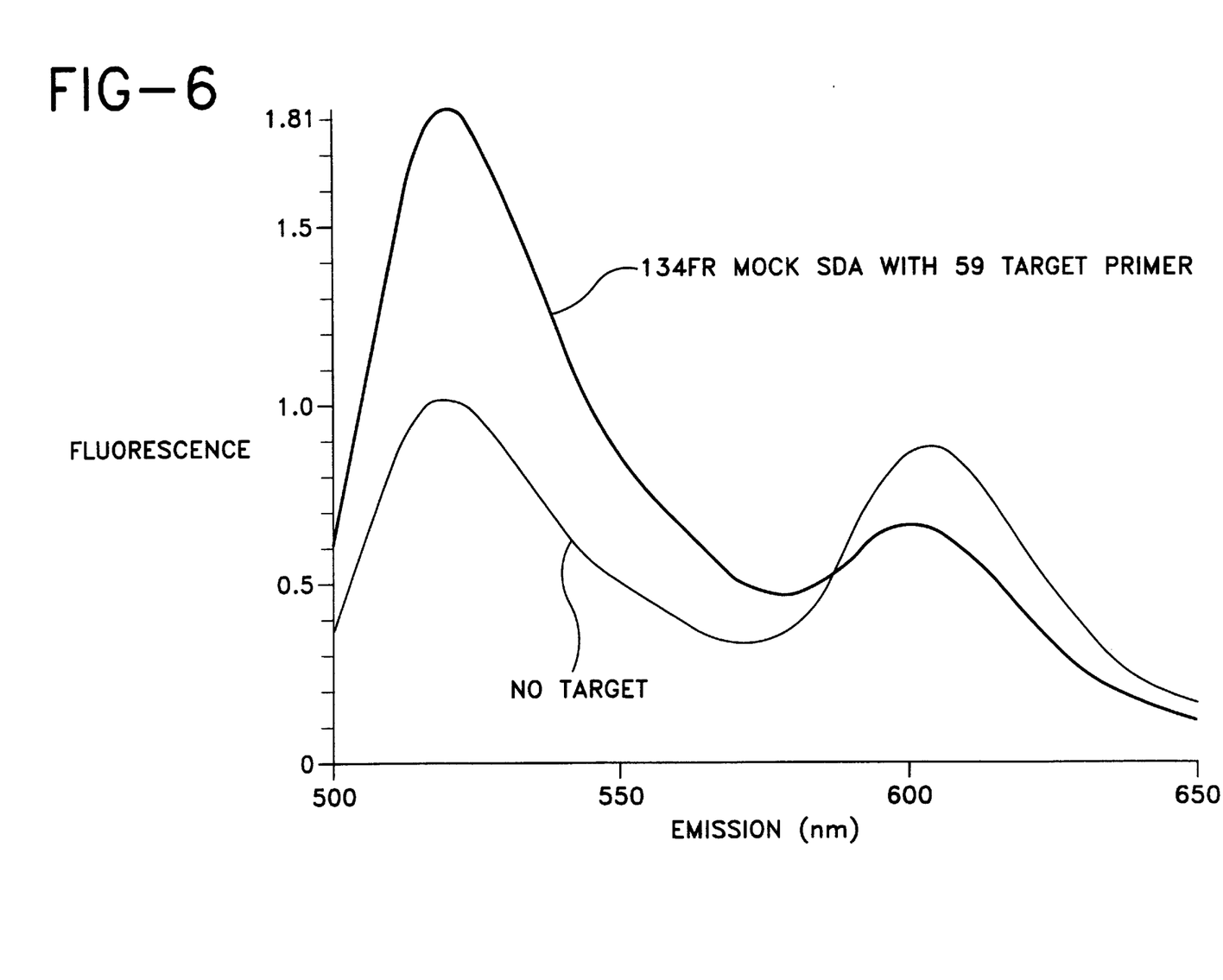
FIG. 6 is a graph illustrating the increase in donor fluorescence when a hybridized primer is extended through a three-tetrad G-quartet structure.

The detector probe was synthesized, labeled and tested in a primer extension assay at 54° C. essentially as described in Example 3. The oligonucleotide complementary to the 3' end of the detector probe was SEQ ID NO:6. Comparison of fluorescence emission at 520 nm in the presence and absence of target is shown in FIG. 6, with an approximately 2-fold increase in donor fluorescence in the presence of target. This is a greater increase in fluorescence than was typically observed using two-tetrad G-quartet detector probes at the same reaction temperature, providing a more sensitive assay.

A second three-tetrad G-quartet detector probe for detection of Chlamydia was synthesized and tested in the primer extension assay described above. Continuous monitoring of the change in fluorescence emission at 520 nm during the primer extension assay revealed approximately a 2-fold increase as the primer was extended on the detector probe to unfold its secondary structure. Comparison of fluorescence emission at static time points before and after primer extension revealed more than a 4-fold increase in fluorescence when this experiment was repeated using a buffer with an increased concentration of potassium ion.

What is claimed is:

1. An oligonucleotide comprising a G-quartet structure, the G-quartet structure comprising two to five G-tetrads and the oligonucleotide being labeled with a donor fluorophore and an acceptor, the donor fluorophore and the acceptor selected such that fluorescence of the donor fluorophore is quenched by the acceptor when the oligonucleotide forms the G-quartet structure and quenching of donor fluorophore fluorescence is reduced upon unfolding or disruption of the G-quartet structure.

2. The oligonucleotide of claim 1 consisting of SEQ ID NO:9, SEQ ID NO:10 or SEQ ID NO:11 labeled with the donor fluorophore and the acceptor.

3. The oligonucleotide of claim 1 wherein the donor fluorophore is fluorescein and the acceptor is Rhodamine-X or the donor fluorophore is Rhodamine-X and the acceptor is Cy5.

4. The oligonucleotide of claim 1 further comprising a wholly or partially single-stranded restriction endonuclease recognition site.

5. A method for detecting or identifying a selected nucleic acid sequence comprising:
   a) providing an oligonucleotide comprising a G-quartet structure and a sequence complementary to the selected nucleic acid, the G-quartet structure comprising two to five G-tetrads and the oligonucleotide being labeled with a donor fluorophore and an acceptor such that fluorescence of the donor fluorophore is quenched by the acceptor when the oligonucleotide forms the G-quartet structure and quenching of donor fluorophore fluorescence is reduced upon unfolding or disruption of the G-quartet structure;
   b) contacting the oligonucleotide with a nucleic acid sample, whereby if the selected nucleic acid sequence is present the oligonucleotide binds to the selected nucleic acid sequence and is rendered double-stranded, thereby unfolding or disrupting the G-quartet structure and reducing quenching of donor fluorophore fluorescence, and;
   c) detecting a change in fluorescence, thereby detecting or identifying the selected nucleic acid.

6. The method of claim 5 wherein the oligonucleotide is rendered double-stranded by hybridization to a complementary sequence.

7. The method of claim 5 wherein the oligonucleotide is rendered double-stranded by synthesis of a complementary sequence using the oligonucleotide as a template.

8. The method of claim 5 wherein the oligonucleotide consists of SEQ ID NO:9, SEQ ID NO:10 or SEQ ID NO:11 labeled with the donor fluorophore and the acceptor.

9. The method of claim 5 wherein the oligonucleotide further comprises a wholly or partially single-stranded restriction enzyme recognition site.

10. The method of claim 5 wherein the donor fluorophore is fluorescein and the acceptor is Rhodamine X or the donor fluorophore is Rhodamine X and the acceptor is Cy5.

11. The method of claim 5 wherein the nucleic acid sequence to be detected or identified is a product of a nucleic acid amplification reaction.

12. The method of claim 11 wherein the nucleic acid sequence to be detected is the product of an SDA reaction.

13. The method of claim 5 wherein an increase in donor fluorescence is detected.

14. The method of claim 5 wherein the acceptor is a fluorophore and a decrease in acceptor fluorescence is detected.

15. The method of claim 5 wherein the oligonucleotide is a signal primer.

16. A method for detecting or identifying a selected nucleic acid sequence comprising:
   a) providing an oligonucleotide comprising a G-quartet structure and a sequence complementary to the selected nucleic acid, the G-quartet structure comprising two to five G-tetrads and the oligonucleotide being labeled with a donor fluorophore and an acceptor such that unfolding or disruption of the G-quartet structure increases the distance between the donor fluorophore and acceptor;
   b) contacting the oligonucleotide with a nucleic acid sample, whereby if the selected nucleic acid sequence is present the oligonucleotide binds to the selected nucleic acid sequence and is rendered double-stranded, thereby unfolding or disrupting the G-quartet structure and increasing the distance between the donor fluorophore and the acceptor, and;
   c) detecting a change in a fluorescence property associated with the increased distance between the donor fluorophore and the acceptor, thereby detecting or identifying the selected nucleic acid sequence.

17. The method of claim 16 wherein a change in fluorescence intensity, fluorescence lifetime, fluorescence polarization or fluorescence anisotropy is detected.

18. The method of claim 16 wherein the oligonucleotide further comprises a wholly or partially single-stranded restriction endonuclease recognition site.

19. A probe comprising a G-quartet structure, the probe being labeled with a donor fluorophore and an acceptor selected such that fluorescence of the donor fluorophore is quenched by the acceptor when the oligonucleotide forms the G-quartet structure and quenching of donor fluorophore fluorescence is reduced upon disruption or unfolding of the G-quartet structure, and the G-quartet structure comprising:
   a) a first oligonucleotide comprising a sequence $G_{2-5}N_xG_{2-5}$ and a second oligonucleotide comprising a sequence $G_{2-5}N_yG_{2-5}$, or;
   b) four oligonucleotides, each of the four oligonucleotides comprising two to five consecutive G residues.

20. A method for detecting or identifying a selected nucleic acid sequence comprising:
   a) providing a probe comprising a G-quartet structure, the probe being labeled with a donor fluorophore and an acceptor selected such that fluorescence of the donor fluorophore is quenched by the acceptor when the oligonucleotide forms the G-quartet structure and quenching of donor fluorophore fluorescence is reduced upon disruption or unfolding of the G-quartet structure, and the G-quartet structure comprising:
      i) a first oligonucleotide comprising a sequence $G_{2-5}N_xG_{2-5}$ and a second oligonucleotide comprising a sequence $G_{2-5}N_yG_{2-5}$, or;
      ii) four oligonucleotides, each of the four oligonucleotides comprising two to five consecutive G residues.
   b) contacting the probe with a nucleic acid sample, whereby if the selected nucleic acid sequence is present the probe binds to the selected nucleic acid sequence, thereby unfolding or disrupting the G-quartet structure and increasing the distance between the donor fluorophore and the acceptor, and;
   c) detecting a change in a fluorescence property associated with the increased distance between the donor fluorophore and the acceptor, thereby detecting or identifying the selected nucleic acid sequence.

21. A probe comprising an i-tetraplex structure, the probe being labeled with a donor fluorophore and an acceptor selected such that fluorescence of the donor fluorophore is quenched by the acceptor when the oligonucleotide forms the i-tetraplex and quenching of donor fluorophore fluorescence is reduced upon unfolding or disruption of the i-tetraplex.

22. A method for detecting or identifying a selected nucleic acid sequence comprising:
   a) providing a probe comprising an i-tetraplex structure, the probe being labeled with a donor fluorophore and an acceptor selected such that fluorescence of the donor fluorophore is quenched by the acceptor when the oligonucleotide forms the i-tetraplex structure and quenching of donor fluorophore fluorescence is reduced upon disruption or unfolding of the i-tetraplex structure;

b) contacting the probe with a nucleic acid sample, whereby if the selected nucleic acid sequence is present the probe binds to the selected nucleic acid sequence, thereby unfolding or disrupting the i-tetraplex structure and increasing the distance between the donor fluorophore and the acceptor, and;

c) detecting a change in a fluorescence property associated with the increased distance between the donor fluorophore and the acceptor, thereby detecting or identifying the selected nucleic acid sequence.

23. A method for detecting or identifying a selected nucleic acid sequence comprising:

a) providing an oligonucleotide comprising an i-tetraplex structure and a sequence complementary to the selected nucleic acid, the oligonucleotide being labeled with a donor fluorophore and an acceptor such that unfolding or disruption of the i-tetraplex structure increases the distance between the donor fluorophore and acceptor;

b) contacting the oligonucleotide with a nucleic acid sample, whereby if the selected nucleic acid sequence is present the oligonucleotide binds to the selected nucleic acid sequence and is rendered double-stranded, thereby unfolding or disrupting the i-tetraplex structure and increasing the distance between the donor fluorophore and the acceptor, and;

c) detecting a change in a fluorescence property associated with the increased distance between the donor fluorophore and the acceptor, thereby detecting or identifying the selected nucleic acid sequence.

* * * * *